US00PP23490P2

(12) United States Plant Patent
MacKenzie

(10) Patent No.: US PP23,490 P2
(45) Date of Patent: Mar. 19, 2013

(54) ***CAMPANULA* PLANT NAMED 'NONOR'**

(50) Latin Name: ***Campanula* hybrid**
Varietal Denomination: Nonor

(75) Inventor: David MacKenzie, Nunica, MI (US)

(73) Assignee: Hortech, Inc., Spring Lake, MI (US)

( * ) Notice: Subject to any disclaimer, the term of this patent is extended or adjusted under 35 U.S.C. 154(b) by 14 days.

(21) Appl. No.: 13/199,010

(22) Filed: Aug. 16, 2011

(51) Int. Cl.
*A01H 5/00* (2006.01)

(52) U.S. Cl. ..... Plt./414

(58) Field of Classification Search ..... Plt./414
See application file for complete search history.

*Primary Examiner* — Kent L Bell
(74) *Attorney, Agent, or Firm* — Penny J. Aguirre

(57) ABSTRACT

A new cultivar of hybrid *Campanula*, 'Nonor', characterized by its numerous flowers that are violet-blue in color, and its height of about 38 cm in bloom.

2 Drawing Sheets

Botanical classification: *Campanula* hybrid.
Cultivar designation: 'Nonor'.

BACKGROUND OF THE INVENTION

The present invention relates to a new and distinct cultivar of hybrid *Campanula* plant, botanically known as *Campanula* 'Nonor' and will be referred to hereafter by its cultivar name, 'Nonor'. The new cultivar represents a new herbaceous perennial grown for landscape use.

The inventor discovered the new cultivar, 'Nonor', as a naturally occurring branch mutation of 'Samantha' (not patented) in July of 2005 in a stock bed in his nursery in Nunica, Mich.

Asexual reproduction of the new cultivar was first accomplished by division in Nunica, Mich. in September of 2005 by the inventor. Propagation has determined that the characteristics of this cultivar are stable and are reproduced true to type in successive generations.

SUMMARY OF THE INVENTION

The following traits have been repeatedly observed and represent the characteristics of the new cultivar. These attributes in combination distinguish 'Nonor' as a unique cultivar of *Campanula*.

1. 'Nonor' exhibits numerous flowers that are violet-blue in color.
2. 'Nonor' reaches a height of about 25 cm and a height of about 38 cm in bloom.

'Samantha', the parent plant of 'Nonor' differs from 'Nonor' in having flowers that are much lighter in color; opening almost pure white (155A with just a slight blush of 85B near petal tips) and maturing to a lighter violet color (N88C) and in being shorter in height. 'Samantha' and 'Nonor' are hybrids of unknown species. Based on habit and flower color, 'Nonor' can be compared to *Campanula carpatica* 'Blue Clips' (not patented). 'Blue Clips' differs from 'Nonor' in having fewer flowers that are larger in size and in having a shorter bloom season.

BRIEF DESCRIPTION OF THE DRAWING

The accompanying colored photographs illustrate the overall appearance and distinct characteristics of the new *Campanula*. The photographs were taken of six month-old plants as grown in one-gallon containers in Nunica, Mich.

The photograph in FIG. 1 provides a view of 'Nonor' in bloom.

Figure 1:
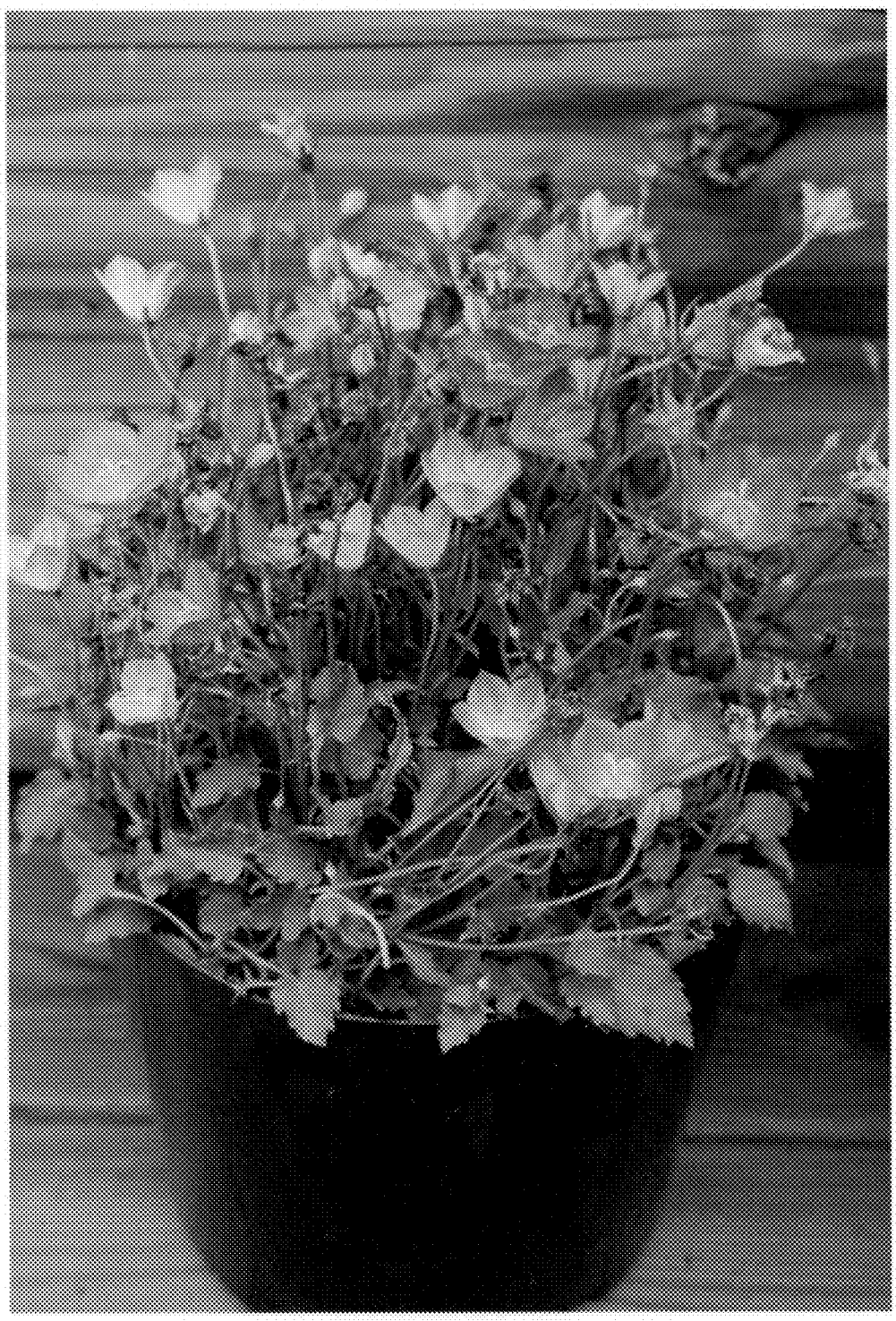
Figure 2:
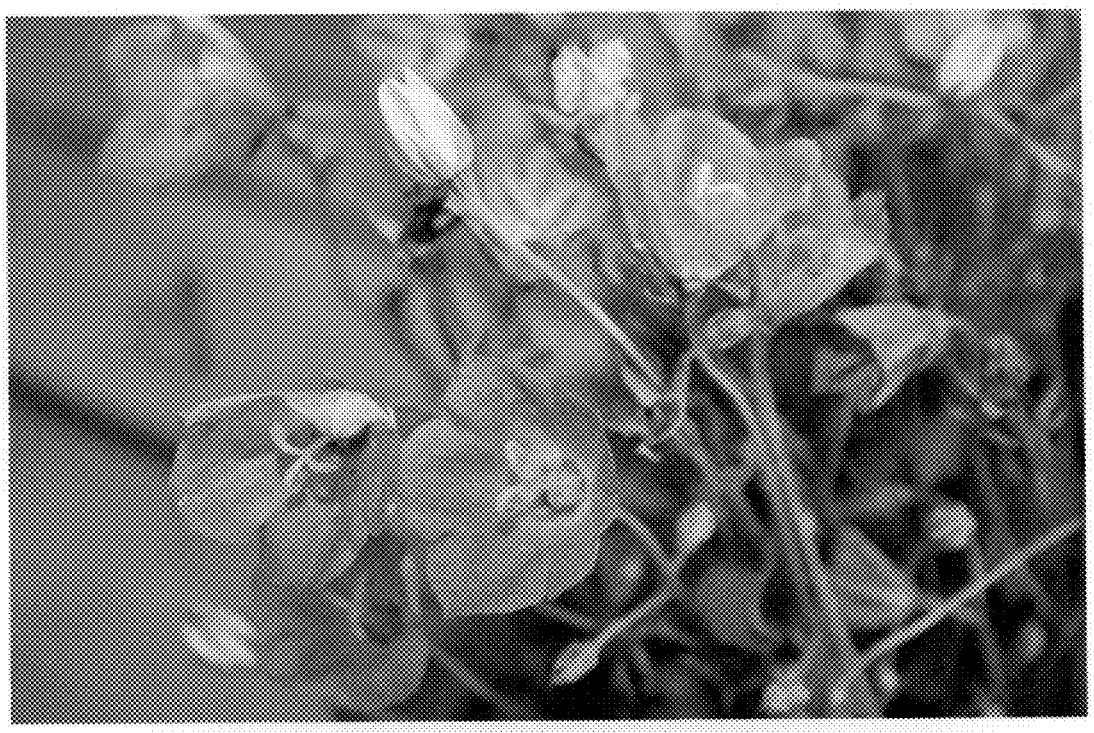

The photograph in FIG. 2 provides a close-up view of the flowers of 'Nonor'.

Figure 3:
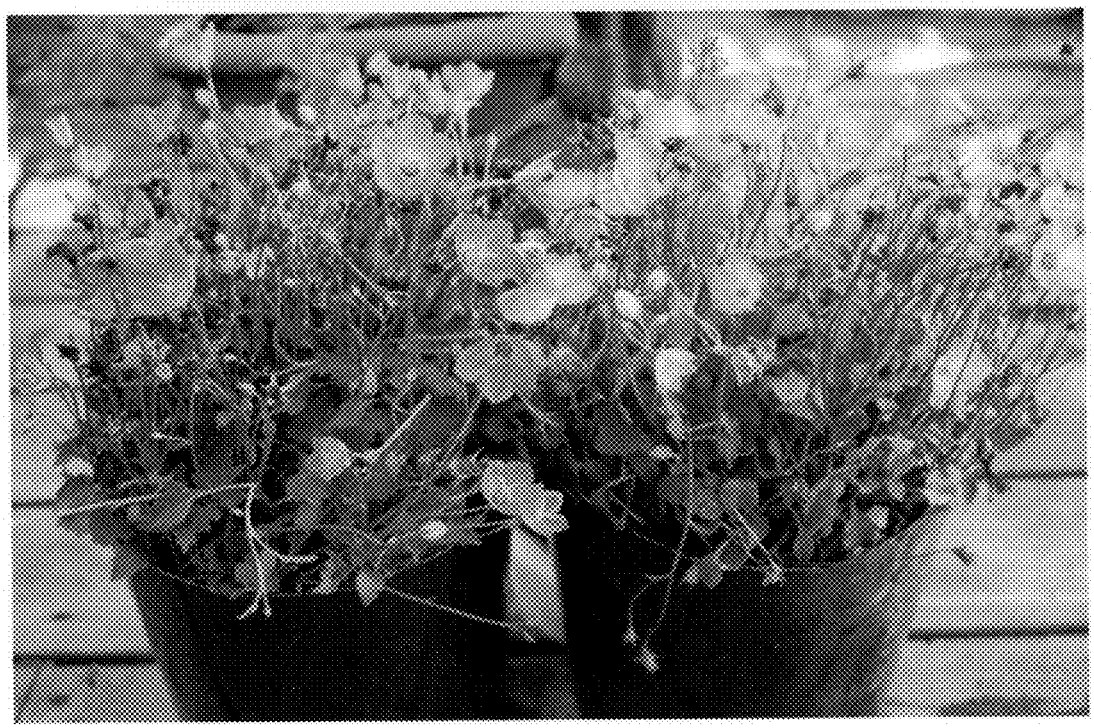

The photograph in FIG. 3 provides a comparison of a plant of 'Nonor' (left) and 'Samantha' (right).

The colors in the photograph may differ slightly from the color values cited in the detailed botanical description, which accurately describe the colors of the new *Campanula*.

DETAILED BOTANICAL DESCRIPTION OF THE PLANT

The following is a detailed description of 6 month-old plants of the new cultivar as grown outdoors in one-gallon containers in Nunica, Mich. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—The last two to three weeks of June to the first or second week of July in Mich.

*Plant habit*.—Herbaceous perennial, dense, low growing, mature plants sprawl from central crown with procumbent stems rooting as they contact the soil.

*Height and spread*.—Reaches about 25 cm in height and about 38 cm in spread.

*Cold hardiness*.—At least in U.S.D.A. Zone 4.

*Diseases and pests*.—No susceptibility or resistance to diseases or pests has been observed.

*Root description*.—Fibrous on creeping rootstocks that are an average of 2 cm in length and 2 mm in width, 145A in color and suffused with 165B.

*Growth rate*.—Moderately vigorous.

*Propagation*.—Division.

Stem description:

*Stem size*.—Average of 15 cm in length (Including peduncles and pedicels) and 2 mm in width.

*Stem shape*.—Round.

*Stem color.*—145A with more mature stems 137B.

*Stem surface.*—Moderately covered with strigose hairs; an average of 1 mm in length, N155A in color.

*Stem number.*—About 30 in a one-gallon container.

*Internode length.*—Branch internodes range from 2 mm to 1 cm, leaf internodes an average of 2 cm.

*Branching habit.*—An average of 7 lateral branches per stem.

Foliage description:

*Leaf shape.*—Ovate to broadly lanceolate.

*Leaf division.*—Simple.

*Leaf base.*—Slightly cordate to truncate.

*Leaf apex.*—Acute-acuminate.

*Leaf venation.*—Pinnate, 145A in color on upper surface and 138B on lower surface.

*Leaf margins.*—Irregularly Serrate and slightly undulated.

*Leaf attachment.*—Petiolate.

*Leaf arrangement.*—Alternate.

*Leaf surface.*—Upper and lower surface; puberulent with a few strigose hairs.

*Leaf color.*—Young and mature leaves; 137B on upper surface and a color between 138A and 138B on lower surface.

*Leaf size.*—Up to 3 cm in length and 2.3 cm in width.

*Leaf quantity.*—Average of 14 per lateral branch.

*Petiole.*—Up to 2.5 cm in length and 1 mm in width, sparsely covered strigose hairs, 145A in color and leafy sides about 0.5 mm in width near leaf blade same color as leaf.

Flower description:

*Inflorescence type.*—Raceme.

*Inflorescence size.*—About 8 cm in length and 4 cm in width on each lateral branch.

*Lastingness of inflorescence.*—About 4 weeks from first flower to last flower in the raceme.

*Lastingness of individual bloom.*—About 7 days.

*Flower size.*—Average of 2.5 cm in height and 2.5 cm in width.

*Flower fragrance.*—None.

*Flower number.*—3 to 5 per lateral branch, an average of 30 per stem.

*Flower aspect.*—Upright to outward.

*Flower bud.*—Average of 1.3 cm in length, up to 5 mm in width (including calyx), oblong in shape, color of petal portion 155C suffused with 86D near apex, color of calyx portion a blend of 144A and 144B.

*Flower form.*—Campanulate.

*Petals.*—5, about 1.5 cm in length and 1 cm in width, upper one-third un-fused and ovate in shape; 1 cm in width and 7 mm in depth, apex cuspidate, base fused, margin entire, surface glabrous on upper and lower surface, color when opening lower surface; 155C suffused with N88C, color when opening upper surface; 155C at base blending into N88C with blush of N88B, color when fully open lower surface; N88C, color when fully open upper surface; a blend of N88B and N88C, color when fully mature lower surface; a blend of N88A and N88B with slight striations of N88C, color when fully mature upper surface; N88A with base N88C.

*Calyx.*—Rotate in form, 1.3 cm in width and 1 cm in depth (including epicalyx), 5-parted with conical shaped epicalyx; about 3 mm in depth and width, finely puberulent surface, color 137A with striations of 138B.

*Sepals.*—5, lanceolate in shape, average of 2 mm in width and 7 mm in length, 137B in color on upper and lower surface, finely puberulent on upper and lower surface, entire margin, base truncate and fused to epicalyx, apex attenuate.

*Peduncles.*—Round in shape, range from 2 to 8 cm in length and 2 mm in width, surface moderately covered with strigose hairs; an average of 1 mm in length, 137B in color.

*Pedicels.*—Round in shape, average of 8 cm in length and 1.5 mm in width, surface glabrous, 137B in color, held upright to an angle of 20° from vertical.

Reproductive organs:

*Gynoecium.*—1 pistil, about 1.8 cm in length, stigma is terete with branches spreading, 5 mm in length, 0.7 mm in width and 144A flushed near apex with 139A, style is about 4 mm in length and 144B in color, ovary is about 2 mm in diameter and 144A in color.

*Androcoecium.*—5 stamens, anthers are basifixed, narrowly oblong in shape, 2.5 mm in length, and about 161A in color, filament is 2 mm in length and 161D in color and attached to a small scale about 2 mm in length and 1 mm in width and 155A in color, pollen is low in quantity and about 161B in color.

*Fruit/seeds.*—Fruit are rounded with a pointed apex, up to 3 mm in length and 6 mm in width, 62A in color, seed production was not observed.

It is claimed:

1. A new and distinct cultivar of *Campanula* plant named 'Nonor' as herein illustrated and described.

* * * * *